United States Patent
Miethke

(10) Patent No.: US 10,675,451 B2
(45) Date of Patent: Jun. 9, 2020

(54) HYDROCEPHALUS SHUNT ARRANGEMENT AND COMPONENTS THEREOF FOR DRAINING CEREBROSPINAL FLUID IN A PATIENT HAVING HYDROCEPHALUS

(71) Applicant: Christoph Miethke, Potsdam (DE)

(72) Inventor: Christoph Miethke, Potsdam (DE)

(73) Assignee: Christoph Miethke GmbH & Co KG, Potsdam (DE)

( * ) Notice: Subject to any disclaimer, the term of this patent is extended or adjusted under 35 U.S.C. 154(b) by 0 days.

(21) Appl. No.: 16/432,490

(22) Filed: Jun. 5, 2019

(65) Prior Publication Data
US 2020/0001058 A1    Jan. 2, 2020

Related U.S. Application Data

(63) Continuation-in-part of application No. 14/988,259, filed on Jan. 5, 2016, which is a continuation of application No. 13/866,730, filed on Apr. 19, 2013, now abandoned, which is a continuation-in-part of
(Continued)

(30) Foreign Application Priority Data

Oct. 22, 2010   (DE) .................. 10 2010 049 150

(51) Int. Cl.
*A61M 27/00*     (2006.01)

(52) U.S. Cl.
CPC ..... *A61M 27/006* (2013.01); *A61M 2027/004* (2013.01); *A61M 2202/0464* (2013.01); *A61M 2210/0693* (2013.01)

(58) Field of Classification Search
CPC .......... A61M 27/006; A61M 2027/004; A61M 2202/0464; A61M 2210/0693
See application file for complete search history.

(56) References Cited

U.S. PATENT DOCUMENTS

| 3,755,059 A | 8/1973 | Calfee |
| 4,407,296 A | 10/1983 | Anderson |
| 4,676,255 A | 6/1987 | Cosman |

(Continued)

FOREIGN PATENT DOCUMENTS

| DE | 19638813 C1 | 3/1998 |
| DE | 19705474 A1 | 8/1998 |

(Continued)

*Primary Examiner* — Philip R Wiest
(74) *Attorney, Agent, or Firm* — Smartpat PLC

(57) ABSTRACT

A hydrocephalus shunt arrangement for draining cerebrospinal fluid (CSF) in a patient includes a ventricle catheter, a first drainage line, a control valve, a second drainage line, and an intracranial device. The ventricle catheter is inserted into a ventricle space of the brain of a patient. The first drainage line is connected to the ventricle catheter. The control valve is connected to the first drainage line and controls the drainage of CSF from the cranium of the patient through the second drainage line into a drainage area inside an abdominal cavity of the patient. The intracranial device is implanted under the skin of the patient in or at the cranium and connected to the ventricle catheter or the control valve. The intracranial device includes a corrugated metal membrane covering a chamber disposed within a rigid housing. The control valve produces a desired, controlled, drainage of excess CSF.

9 Claims, 8 Drawing Sheets

Related U.S. Application Data application No. PCT/EP2011/003903, filed on Aug. 4, 2011, now abandoned.

(56) References Cited

U.S. PATENT DOCUMENTS

| | | | |
|---|---|---|---|
| 4,738,267 | A | 4/1988 | Lazorthes et al. |
| 5,350,307 | A | 9/1994 | Takagishi et al. |
| 5,777,610 | A | 7/1998 | Sugimoto et al. |
| 5,951,487 | A | 9/1999 | Brehmeier-Flick et al. |
| 5,983,726 | A | 11/1999 | Heller |
| 6,113,553 | A | 9/2000 | Chubbuck |
| 6,673,022 | B1 | 1/2004 | Bobo et al. |
| 7,037,277 | B1 | 5/2006 | Smith et al. |
| 7,422,566 | B2 | 9/2008 | Miethke |
| 7,568,394 | B1 | 8/2009 | Keilman et al. |
| 7,766,855 | B2 | 8/2010 | Miethke |
| 7,785,268 | B2 | 8/2010 | Miethke et al. |
| 8,870,809 | B2 | 10/2014 | Miethke |
| 2002/0047954 | A1 | 4/2002 | Brandt et al. |
| 2003/0139699 | A1* | 7/2003 | Rosenberg .......... A61M 27/006 604/9 |
| 2004/0070721 | A1 | 4/2004 | Tsubokura et al. |
| 2004/0228089 | A1 | 11/2004 | Luebs |
| 2006/0040417 | A1 | 2/2006 | Eldridge et al. |
| 2006/0048580 | A1* | 3/2006 | Vogler ................ G01L 19/0084 73/706 |
| 2006/0086532 | A1 | 4/2006 | Ho et al. |
| 2007/0004999 | A1 | 1/2007 | Miethke |
| 2007/0093741 | A1 | 4/2007 | Miethke |
| 2007/0191717 | A1 | 8/2007 | Rosen et al. |
| 2008/0055079 | A1 | 3/2008 | Fraden |
| 2008/0139959 | A1 | 6/2008 | Miethke et al. |
| 2008/0168483 | A1 | 7/2008 | Chen |
| 2008/0262319 | A1 | 10/2008 | Reichenberger et al. |
| 2008/0314189 | A1 | 12/2008 | Lutz |
| 2010/0030103 | A1 | 2/2010 | Lutze et al. |
| 2010/0218442 | A1 | 9/2010 | Matheisl et al. |
| 2011/0009716 | A1 | 1/2011 | Gohler et al. |
| 2011/0113889 | A1 | 5/2011 | Funken et al. |
| 2011/0166495 | A1 | 7/2011 | Miethke et al. |
| 2012/0010476 | A1 | 1/2012 | Chambers |
| 2012/0232462 | A1 | 9/2012 | Miethke |

FOREIGN PATENT DOCUMENTS

| | | |
|---|---|---|
| DE | 19858172 A1 | 6/2000 |
| DE | 10156494 A1 | 6/2003 |
| DE | 10239743 A2 | 3/2004 |
| DE | 102004015500 A1 | 1/2006 |
| DE | 102005008454 A1 | 8/2006 |
| DE | 102005020569 A1 | 11/2006 |
| DE | 102007008642 | 8/2008 |
| DE | 102007024270 A1 | 11/2008 |
| DE | 102007056844 A1 | 6/2009 |
| DE | 102008011601 A1 | 9/2009 |
| DE | 102008030942 A1 | 1/2010 |
| DE | 102008033337 A1 | 1/2010 |
| DE | 102008037736 A1 | 2/2010 |
| DE | 102009060533 | 7/2019 |
| EP | 1312302 A3 | 3/2004 |
| JP | S5770303 A | 4/1982 |
| JP | S63274832 A | 11/1988 |
| JP | H0550337 B2 | 7/1993 |
| JP | H09145512 A | 6/1997 |
| JP | 2002107246 A | 4/2002 |
| JP | 3316555 B2 | 8/2002 |
| JP | 2005249512 A | 9/2005 |
| JP | 2008539811 A | 11/2008 |
| JP | 4778040 B2 | 9/2011 |
| WO | 2004052443 A1 | 6/2004 |
| WO | 2005092424 A1 | 10/2005 |
| WO | 2006117123 A1 | 11/2006 |
| WO | 2008101563 A1 | 8/2008 |
| WO | 2010000461 A1 | 1/2010 |
| WO | 2010040189 A1 | 4/2010 |
| WO | 2011076382 A1 | 6/2011 |

* cited by examiner

HYDROCEPHALUS SHUNT ARRANGEMENT AND COMPONENTS THEREOF FOR DRAINING CEREBROSPINAL FLUID IN A PATIENT HAVING HYDROCEPHALUS

BACKGROUND

1. Technical Field

The present application relates to a hydrocephalus shunt arrangement and components thereof for draining cerebrospinal fluid in a patient having hydrocephalus. The present application also relates to a percutaneously adjustable drainage system for cerebrospinal fluid. The present application also relates to a subcutaneously implantable hydrocephalus shunt system.

2. Background Information

Hydrocephalus, or water on the brain, is a medical condition requiring treatment using different drainage devices and methods, examples of which are disclosed in the following U.S. Pat. Nos. 8,870,809; 7,422,566; and 7,766,855.

In medicine, a connection between normally separated vessels or cavities is called a shunt. Various synthetic shunts are known. Malformations that occur in nature and likewise make a connection between vessels or cavities are not considered in the following use of the term shunt.

Shunts between the arterial and venous circulatory system may be important. This type of shunt may serve to improve the oxygen supply of the patient.

With dialysis patients, a shunt is implanted in order to develop a high volume vessel for hemodialysis.

A shunt may be provided between the Areteria radians and the Vena cephalica on the forearm.

For patients with kidney damage, dialysis shunts may be essential for survival.

In neurosurgery with hydrocephalus cases, the shunt may be of major importance for draining off the liquor. This is mostly a tube or passage led subcutaneously from the cranium down through the throat into the upper vena cava or from the thoracic wall to the abdominal cavity.

There are also various other shunts of lesser importance.

Shunts provided for hydrocephalus may be provided with a valve in order to control or regulate the discharge of the liquor in the shunt. More recently, adjustable valves may be used. The drain liquid is then the liquor.

Various ailments of the patients can be alleviated not only by liquid discharge, but also through treatment with medicaments or pharmaceuticals, and possibly eliminated and/or reduced and/or minimized.

Cerebrospinal fluid drainage is required and/or desired for example for hemorrhages resulting from a head injury or for cerebral hemorrhages resulting from an aneurysm. Cerebrospinal fluid drainage is also frequently used for equalizing the pressure or decreasing the pressure in hydrocephalus patients.

Cerebrospinal fluid drainage influences the pressure conditions in the intracranial cavity of the patient and prevents, minimizes, and/or restricts any damage to the brain from excessive intracranial pressures.

Internal and external drainage are used for pressure equalization/reduction. The cerebral fluid must only or should flow away in a controlled or substantially controlled manner. An uncontrolled discharge is just as dangerous as an excessive pressure. The discharge of the cerebrospinal fluid is controlled by means of a valve.

Hydrocephalus patients have the following medical problem: the brain is surrounded by a special liquid called liquor. This liquor is formed in symmetrically located chambers of the brain, flows through ventricles into the outer subarachnoid space, where it is resorbed. Normally there exists equilibrium between the amount of fluid that is produced and the amount that is resorbed. In the illness hydrocephalus (also called water on the brain), this equilibrium is disrupted and a sufficient amount of fluid is no longer resorbed. This condition results in an increase in pressure inside the patient's head. In infants, this condition results in abnormal growth of the head; the brain decreases in size and the interior of the patient's skull is increasingly filled only with liquor. In adults, no further growth of the head is possible and critical pressure levels are reached quickly. The brain is weakened by the presence of the excess fluid. In adults, this condition can cause problems in the patient's gait, urinary incontinence, and dementia.

Since the 1950s, hydrocephalus has been treated successfully by the implantation of an artificial drainage system. In this case, an artificial connection is created between the chambers in the brain and a drainage medium. As a rule, the peritoneum (the abdominal cavity) is currently most often used. Alternatively, drainage into the right atrium of the heart is also conventional. Special valves are integrated into these systems, the purpose of which is to control the drainage of fluid. Since the introduction of artificial drainage in hydrocephalus therapy in the early 1950s, numerous different valve systems have been proposed to optimize the result of the treatment.

In recent years, the attention of specialists in the field has been increasingly focused on two competing valve designs: on one hand, percutaneous adjustable valves in which the opening characteristic can be adjusted to individual patient requirements, and on the other hand valves that guarantee an opening characteristic that varies as a function of the position of the valve.

Valve systems of the latter type have a significantly higher opening pressure when the patient is in the standing position than in the reclining position. Both valve systems are currently used with great success for the treatment of hydrocephalus.

Recording the intracranial pressure is of the utmost importance in the context of neurosurgical interventions.

The solution to this problem has been the object of numerous inventions; however, the systems available up to now have serious disadvantages. At least one object of a possible embodiment according to the present application may be to overcome these disadvantages.

In clinical practice, invasive measurement techniques, in which a sensor is inserted into the body, have gained acceptance, wherein the signal is transmitted over a cable link to an external device for displaying and analyzing the measured value. This often happens in conjunction with a synthetic drainage line, through which cerebrospinal fluid is intended to be extracorporeally drained. The very high risk of infection is critical with such systems. Long treatment periods can be realized with very costly infection prophylaxis and the repeated exchange of the pressure sensor. However, with patients suffering from hydrocephalus, it may be the extra-clinical course of the intracranial pressure which is of great diagnostic interest once an internal synthetic drainage system has been implanted. For such tasks, suitable systems are those that transmit the measurement signal through the intact skin or even permit the measurement through the skin.

OBJECT OR OBJECTS

The present application addresses deficiencies in hydrocephalus shunt systems for draining cerebrospinal fluid.

SUMMARY

The object is achieved according to at least one possible embodiment of the present application.

The features of the present application include a corrugated, very special membrane, wherein the dimensions of the corrugations and the membrane thickness play a considerable role.

According to the present application, a pressure chamber is used that is filled with a fluid, in one possible embodiment a gaseous medium, and is separated on one side from the exterior by a membrane that is in one possible embodiment made of a metal. The overall construction, comprising pressure chamber, sensor technology, evaluation, telemetric transmission and energy source, is located in a housing. This may make it unnecessary and/or undesired for any functioning part to be guided into the area of the central nervous system. Ventricle catheters are suitable, as are usually used in shunt systems for treating hydrocephalus.

The operational principle of the gaseous pressure mediator can be described as follows:

A change in the pressure outside the container causes a deformation of the membrane which is determined by the volume in the container, the characteristics of the membrane and the value of the externally acting pressure change.

With a cylindrical housing, for example a cylindrical catheter with a membrane located on the circumference, the pressures within and outside the container can differ due to the stresses in the membrane which result from the curvature. Indeed, for each membrane position there is then a characteristic pressure situation in the container which corresponds to an externally applied pressure. Consequently, the external pressure can be inferred by measuring the pressure in the container. The movement of the selected membrane is not linearly dependent on the applied pressure difference.

If the membrane is located on the end face of a cylindrical housing, then for a flat end surface there is a possible membrane position, in which the membrane likewise forms a flat surface. In other membrane positions, the membrane possesses a curvature (convex or concave), for which comparable rules apply as for a membrane located on the circumference of a cylindrical housing.

According to the present application, one possible flexibility of the membrane surface is achieved through a corrugated surface of the membrane surface. At least one corrugation in the membrane surface is provided. In at least one possible embodiment of the present application, at least one-third of the pressure-impacted membrane surface is corrugated, in another possible embodiment at least two-thirds of the pressure-impacted membrane surface and in yet another possible embodiment of the present application at least four-fifths of the pressure-impacted membrane surface is corrugated. "Pressure-impacted surface" here is the membrane surface that is impacted by an external medium, by the cerebrospinal fluid or liquor. The membrane can be relatively easily deformed at the corrugations, in any respect much easier than a smooth/flat film in the initial state. In this way the membrane according to the present application may contribute to a more reliable and drift-free measurement of body pressures, even for long periods of time, even for miniaturized microchip sensors that are produced on a silicon basis.

If one wants to carry out an indirect pressure measurement by measuring the pressure in a container, then in one possible embodiment of the present application the chamber may comprise a membrane that is stress-free for the most frequently applied pressure. The stress-free membrane is not under tension. The lower the stresses that occur in the membrane with external pressure fluctuations, the more accurate the pressure is transferred from outside to inside and the more accurate is the measurement. In the best case, the pressure to be measured never reaches a value that causes significant stresses in the membrane. Depending on the characteristics and shape of the membrane, no changes or very minor changes in stress occur within the membrane. With the resilient membrane of the present application, the stresses in the membrane can be minimized.

The smaller the membrane surface, the greater is the influence of the membrane stiffness on the measuring procedure.

The pressure chamber can be designed such that the membrane at maximum deflection or at maximum deformation does not touch an opposite chamber wall.

In one possible embodiment of the present application, however, the distance of the membrane from the opposite chamber wall is selected such that the opposite chamber wall limits the curvature of the membrane. The opposite chamber wall then forms a membrane contact surface/touching surface.

The membrane contact surface can have various shapes, flat and/or curved, funnel-shaped or hill-shaped. In the case of a flat membrane contact surface the membrane, in the case of an intended contact, initially touches the center of the opposite chamber wall. With a centrally arranged gas line that supplies the pressure sensor, in the extreme case this immediately and/or substantially immediately closes the gas line and interrupts the pressure measurement. If an additional measurement is intended in spite of the central contact, then various measures can be considered for this. The gas line is optionally displaced such that it discharges more on the edge of the membrane into the gap between membrane and membrane contact surface.

The membrane contact surface is in one possible embodiment of the present application designed such that the first contact of the membrane with the membrane contact surface does not occur centrally but rather at a distance from the center. This is the case for example with a funnel shape. A gas volume then remains at the center. Matching the shape of the bulging membrane can minimize the gas volume.

Alternatively or in addition, the membrane contact surface can be provided with slight indentations that cause a continued connection of the gap between membrane and membrane contact surface with the gas line that leads to the pressure sensor.

It should be taken into account that the membrane is differently deformed depending on the applied pressure. In at least one possible embodiment of the present application, the membrane contact surface may be matched to a selected deformation state of the membrane. Matching a corrugated membrane in one possible embodiment leads to a corrugated membrane contact surface. According to the deformation to the membrane, the membrane contact surface possesses a corrugation, with which the membrane contact surface is substantially totally or partially closingly applied on the membrane in the selected deformation state of the membrane, and fills out the indentations of the membrane between the ridges of the corrugations.

The pressure sensor can be integrated in the membrane contact surface. In this case a slight gap is in one possible embodiment of the present application preserved between the membrane and the pressure sensor.

The pressure sensor is in at least one possible embodiment of the present application located in another chamber that is spaced apart from the pressure chamber (with the membrane), this other chamber being connected with the space between corrugated membrane and membrane contact surface by a lead. The volume of the pressure chamber is constructively defined by the construction space and can be divided up into a passive and an active space. In this regard the active space is that space which can be displaced to a maximum by the membrane at an applied overpressure, i.e. the swept volume. The pressure sensor is found in the remaining unchangeable part of the chamber volume, in the passive space.

In one possible embodiment of the present application, the passive space may be greater than the active swept volume.

However, the pressure measurement according to the present application is also possible when the passive space is greater than the active swept volume.

A partial surface contact of the membrane on the membrane contact surface is harmless.

With a very rigid membrane without corrugations, an important point for the achievement of a sufficient measurement accuracy is that the passive part of the chamber volume is very much smaller than the active swept volume, in one possible embodiment the ratio being greater than 1:10. As a small chamber volume is also wished for, laborious designs for a rigid membrane are necessary and/or desired in order to minimize the chamber volume in relation to the active swept volume.

Those requirements are much reduced for the flexible membrane of the present application. In at least one possible embodiment of the present application, the swept volume may be greater than the passive space. When using the corrugated membrane of the present application, it can also be satisfactory if the passive chamber is greater than the active swept volume. In this regard the ratio is in one possible embodiment 4:1, in another possible embodiment the ratio 2:1 may not exceeded. The membrane surface is favorably adjusted to the chamber volume. In one possible embodiment results are obtained for the circular membrane surface when the ratio of height of the membrane stroke to the radius of the membrane surface is 1:15 to 1:50, in one possible embodiment 1:25 plus/minus twenty percent (relative to 1/25). With otherwise shaped membranes comparable results can be expected if the average radius of the membrane surface to the membrane stroke is kept to this ratio.

The total volume of the chamber is in one possible embodiment fifty to three hundred cubic millimeters. This does not exclude other volumetric sizes of the chamber. For example, in one possible embodiment of the present application, the chamber may comprise a structural shape having approximately one hundred thirty cubic millimeters chamber volume and forty cubic millimeter stroke volume. In the given size range of the chamber volume, the membrane stroke volume may be approximately twenty to one hundred cubic millimeters. The introduction of the flexible membrane of the present application facilitates the technical feasibility, as the larger chamber volume of the overall and in one possible embodiment the larger passive area leaves sufficient space for the installation of the required and/or desired system components.

The membrane is in one possible embodiment round, although other shapes are also possible, from oval to polygonal variants. The membrane surface is in one possible embodiment circular. For other structural shapes the suitable size ratio of stroke height:radius may be determined by back calculation or simplification to a circular surface.

A spiral or circular or other type of corrugation can be provided for the membrane. Spiral corrugations can be single threaded or multi-threaded. Circularly running corrugations are in one possible embodiment provided. Circularly running corrugations show a deformation behavior in one possible embodiment. With a plurality of circular corrugations, the corrugations are in one possible embodiment provided with a different circular diameter, such that a concentric design is possible. In this regard, if a corrugation connects to another, the diameter at each corrugation center of a corrugation circle is two times the corrugation size larger than the enclosed adjacent corrugation circle. If a gap is also provided between the corrugations then the diameter at each corrugation center is increased in relation to the preceding diameter by two times the gap size.

The cross sections of the corrugations can have different shapes. In the extreme case the corrugation can simply be a bulge in one or another direction perpendicular or substantially perpendicular to the membrane film plane. A sinusoidal corrugation path is in one possible embodiment provided with a bulge in the one direction, a bulge in the other direction perpendicular or substantially perpendicular to the membrane film plane. This means that the corrugation in one possible embodiment runs like a sine wave vibration. Another path can also be considered when the corrugation at its ridge and furrow is rounded, the radius of which is at least equal to multiple thicknesses of the membrane film, in one possible embodiment at least equal to ten times the thickness of the membrane film, in another possible embodiment at least equal to fifty times the thickness of the membrane film, in yet another possible embodiment at least equal to one hundred times the thickness of the membrane film.

In this regard, the titanium membrane film can have a low thickness of 0.005 to 0.05 millimeter, ine one possible embodiment a thickness of 0.01 to 0.03 millimeter.

The corrugated membrane contributes to a reduced active stroke volume when the corrugated membrane can be deformed against a corrugated surface (membrane contact surface), such that the membrane having a bulge can be inserted into an indentation of the membrane contact surface and conversely the membrane contact surface can lay with a bulge in the indentations of the membrane. Favorable conditions already result when the membrane contact surface has a similar corrugation as the membrane. Even better conditions result when the contour of the membrane contact surface is copied from the shaped membrane. The membrane suffers a change in shape by the impact of the pressure. If the membrane contact surface is matched to it, then the volume between membrane and pressure sensor can be minimized. The maximum deflection of the membrane can be limited in this way such that an elongation of up to nearly the yield stress of the material is allowed. The maximum elongation is therefore dependent on the size of the membrane and can be up to one millimeter, in one possible embodiment 0.005 to 0.04 millimeter, in another possible embodiment 0.01 to 0.03 millimeter. This enables a very large measurement range for the applied pressure. For low thicknesses the membranes are produced from films. For greater thicknesses they are produced from sheets.

With the pressures that arise in the context of an intracranial pressure measurement, the membrane should work in a state that is as unstressed as possible. For pressures in the range of 800 to 1200 millibar the membrane of one possible design should not touch the contact surface.

As the membrane is deformed inwards, this is initially valid for overpressures. Operationally there is no difference whether there is an over- or under-pressure; the construction allows both situations to be recorded with the same measurement accuracy. If the convex curvature of the membrane is limited by a corrugated contact surface that is likewise matched to the membrane, then an optimal shaping is also essentially ensured or promoted here up to the yield point of the material.

Such high pressures do not occur in the implanted state, although such forces can be found in the manufacturing process and here in one possible embodiment during sterilization. The robustness of the construction allows in one possible embodiment economic sterilization by means of steam, involving very high pressures of up to two hundred bar.

Depending on the arrangement of the membrane film on the housing, it may be required and/or desired to deform the membrane at the edge as well. This is the case, for example with a cylindrical housing that is sealed by the membrane on the end face. It can then be possible to produce, in addition to the corrugation, another collar on the membrane, with which the membrane is guided around the edge of the end face to the housing cover when closing the end face housing opening.

The housing of the measurement cell, apart from the surface formed by the membrane, is rigid and sealed or substantially sealed or at least partially sealed. In addition to the pressure chamber, the housing comprises the pressure sensor, in one possible embodiment in the form of an ASIC chip (electronic circuit, comprising digital components and the connections between them), as well as electronic components for the analysis, telemetric transmission and energy supply. The energy is supplied inductively; a coil is incorporated for this in the housing. A battery can likewise be employed.

The pressure sensor is very sensitive to mechanical stress. If the chip were subjected to a mechanical stress then the measurement results would be of no use. A strain-free arrangement is therefore desirable. Mechanical stresses can result from stresses in the installation, by movement or by thermal expansion of the components. In one embodiment of the present application, the chip is assembled on its own circuit board. The chip is in one possible embodiment fixed by means of punctual adhesive bonding at the center of the chip. The chip has contact points on two opposite sides, the points in one possible embodiment being connected to the base board by bonding. The bonded connections are in one possible embodiment protected by a Glop Top casting resin (heat-curable epoxy resin). In addition to the ASIC pressure sensor chip, there are in one possible embodiment the capacitors for the voltage control on the base board, such that three conductors are required and/or desired to connect the whole board with the remaining electronics. The punctual, central adhesive bonding of the chip and the flexible connection by bonding essentially ensures and/or promotes that the stress on the chip by mechanical stresses is already very well decoupled from the base board.

The base board itself is also slit at two places on the long sides at the height of the edges of the ASIC chip. In this way a difference in the thermal expansion of the base board to the chip and its connections is equalized. The base board can be manufactured from ceramic which has a similar expansion coefficient to that of the chip; in one possible embodiment FR4 can be used with a thickness of 0.5 millimeter.

An additional decoupling of the base board may also be possible. This may be achieved by suspending one side of the base board on the main board of the measuring cell. It is suspended on the same side as that on which the wirings of the connecting cable of the ASIC lay. These cables themselves are twisted in a spiral, such that no mechanical resistance results and the connection is very elastic.

The assembly of the pressure sensor chip according to the present application and the base board essentially ensures and/or promotes a completely strain-free suspension. One possible embodiment of the circuit board is shown in FIG. 5.

In order to also essentially ensure and/or promote added protection against shocks and to minimize the volume of the chamber of the measurement cell, the measurement cell is additionally filled up or in one possible embodiment potted. Here, the pressure sensor itself is not potted. The thus obtained direct contact with the pressure transfer medium affords a high dynamic resonance of the measurement, as no interfering attenuation exists between medium and sensor chip. The gap between the chip and the filling template can be kept very small, it is in one possible embodiment less than 0.01 millimeter.

In order to prevent and/or minimize and/or reduce the filling material from degassing once the measurement cell is sealed, and to cure the material in a controlled manner, the cell is cured prior to mounting the membrane. This is accomplished by heating the cell for some hours at sixty to one hundred fifty degrees Celsius. Once the membrane is mounted, thereby irreversibly sealing the measurement cell, the aging of the filling material can no longer be influenced. This is noncritical, as the filling serves exclusively to protect the sensitive components and to minimize the gas-filled chamber volume.

The inventively corrugated metal membrane is in one possible embodiment deep drawn when cold. For this the material is deformed past its elastic yield point, such that a permanent or substantially permanent deformation results. The deformation can be carried out in a press between appropriately shaped matrix and insert. The deformation can also be carried out with a liquid or gaseous applied pressure that presses the film against or into a mold. The matrix surface or insert surface or mold surface required and/or desired for this can be determined with a few experiments, in which the recesses for shaping the membrane film in the matrix or insert or mold surface are deepened until the membrane, after deformation, shows the desired corrugations.

Permanent and/or substantially permanent deformation when cold is difficult with plastics, because plastic when cold, depending on its nature, shows an extremely high elastic deformation. However, plastic membranes made of thermoplastic material can be softened by heating them. A permanent or substantially permanent deformation is easily achieved in the softened state.

The additional membrane deformation can optionally be carried out before the corrugation, substantially simultaneously with the corrugation or after the corrugation.

To incorporate the membrane, it is positioned on a window in the housing of the measurement cell and then in one possible embodiment welded to this housing. This is possible both for plastic parts as well as for metallic parts, also for housing and membrane made of titanium. In this regard, an external surface of the housing is in one possible embodiment selected as the weld position. The membrane can be held in the welding position on the external surface with rings or sleeves. The rings and sleeves can simply be assembly aids and can be removed after welding or can remain in place.

In at least one possible embodiment of the present application, it may be possible to use liquids to embed the measurement device. In yet another possible embodiment of the present application, gaseous media may be employed as the pressure medium/pressure mediator. Metallic membrane films, in one possible embodiment made of titanium, are gas-tight. This is not the case for plastic membranes. With the latter, diffusion of the gas through the plastic membrane is to be expected.

According to the illustrated embodiment, after the membrane has been welded the measurement cell is completely sealed and tightly hermetically encapsulated. None of the electronic components, leads, fillers or seals of the cell come into contact with the medium to be measured and cannot affect the measurement.

The measurement cell is in one possible embodiment incorporated as a sealed unit into a housing. The measurement cell can be placed on the tip of a catheter; in one possible embodiment it concerns a valve housing that is to be implanted extracranially. A possible design shows a measurement cell combined with a burrhole reservoir. The reservoir housing comprises a proximally located supply line, a distal drainage, an interior space that comprises the measurement cell as well as a reservoir chamber. The housing is sealed and comprises up to the top side of a solid, hermetically sealed and biocompatible material. The material for this can be a metal, in one possible embodiment titanium, in one possible embodiment a suitable, non-metallic material, in another possible embodiment a polyaryl ether ketone, in yet another possible embodiment polyether ether ketone (PEEK). A non-metallic housing has the least influence on the inductive energy supply and the telemetric data transmission. The possible distance of the display device (not described here) away from the implant is increased hereby for example by up to ten centimeters. As the housing otherwise has no influence on the operation of the measurement cell and also may not otherwise satisfy mechanical demands, a non-metallic material can be employed.

The top side of the housing comprises a cover made of a polymeric material, in one possible embodiment silicone.

In at least one possible embodiment of the present application, the pressure sensor and a burrhole reservoir may be combined. The pressure sensor can be completely integrated into an already existing shunt system, meaning that an additional implant is not required and/or desired. In this way the pressure that is actually relevant for the diagnosis is measured at the same time as that which also applies to the drainage direction downstream of the implanted hydrocephalus valve. Shunt systems are often fitted with burrhole reservoirs that take on the required and/or desired redirection of the catheter on leaving the cranium and possess a similarly constructed silicone cover. Reservoirs of this type are found for example in the product catalog of the company Christoph Miethke GmbH & Co. KG. This enables a syringe to be used externally to remove liquor directly or to introduce medicaments. For this, the cover can be pierced directly through the skin.

The measurement cell can be integrated into the housing in such a way that the flexible membrane on the lower side of the housing faces upwards and therefore the solid lower side of the measurement cell faces away from the cover. In this way the lower side serves as a protection and a limit when the cover is pierced with a syringe.

Other combinations can also be considered, e.g. a combination of the pressure measurement cell with a hydrocephalus valve.

The corrugated membrane finds on the lower side of the housing an opposite side that has a correspondingly shaped corrugation. Under a negative pressure the membrane is deformed until it lies on the lower side, whereupon a measurement range results at about the same level as for an external overpressure. Negative pressures of this magnitude indeed never exist in operation, but can occur in the manufacturing process depending on the manufacturing process.

The present application is in one possible embodiment suitable for pressure ranges, in which an essentially stress-free or low-stress displacement of the membrane occurs.

Fundamentally, various measurement locations are established for the intracranial pressure measurement. The intraventricular measurement is possible; for the parenchymal, the epidural or the subdural measurement, embodiments are likewise obvious.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

As discussed above, hydrocephalus patients have the following medical problem: the brain is surrounded by a special liquid called liquor. This liquor is continuously being produced and reabsorbed in equal amounts. In the illness hydrocephalus (also called water on the brain), this equilibrium is disrupted and more liquid is produced than is reabsorbed. Because the interior of the skull represents a closed vessel, the result is an increase in volume. In infants, the seams in the skull cannot grow together and close, and in adults the internal pressure in the skull increases. Therefore there are two varieties of hydrocephalus: adult and infantile.

Hydrocephalus treatment initially consisted of simply draining the liquor. This drainage was effected by means of a simple hose connection between the skull and a large blood venous blood vessel or by a corresponding connection between the skull and the abdomen via a hose. It was quickly determined, however, that the pressure in the skull must maintain a certain physiological value if other complications are to be prevented.

In the treatment of hydrocephalus, implantable drains are used to create an artificial connection between the ventricles of the brain in the head and a drainage compartment, which is currently most often the abdomen.

A number of different types of valves are known that are installed in the drain for the liquor, and by means of which the pressure of the liquor can be set. Valves of this type are implanted under the skin in the vicinity of the head. The valves are designed to open at a certain critical pressure and to release the flow of liquor. By means of a line—which is also implanted under the skin—the liquor is drained into the upper vena cava or into the abdominal cavity.

The valves in question are implanted in the patient and preferably drain the excess liquor from the patient's skull via a hose, which is likewise implanted, and empty into the vena cava or into the abdomen. The valve pressure is thereby determined by a spring, whereby the spring is adjusted by means of a mechanism that has a pivoting or rotating part that is moved from outside by pivoting or rotating an integrated magnet, so that the tension on the spring is increased or relaxed.

Figure 1:
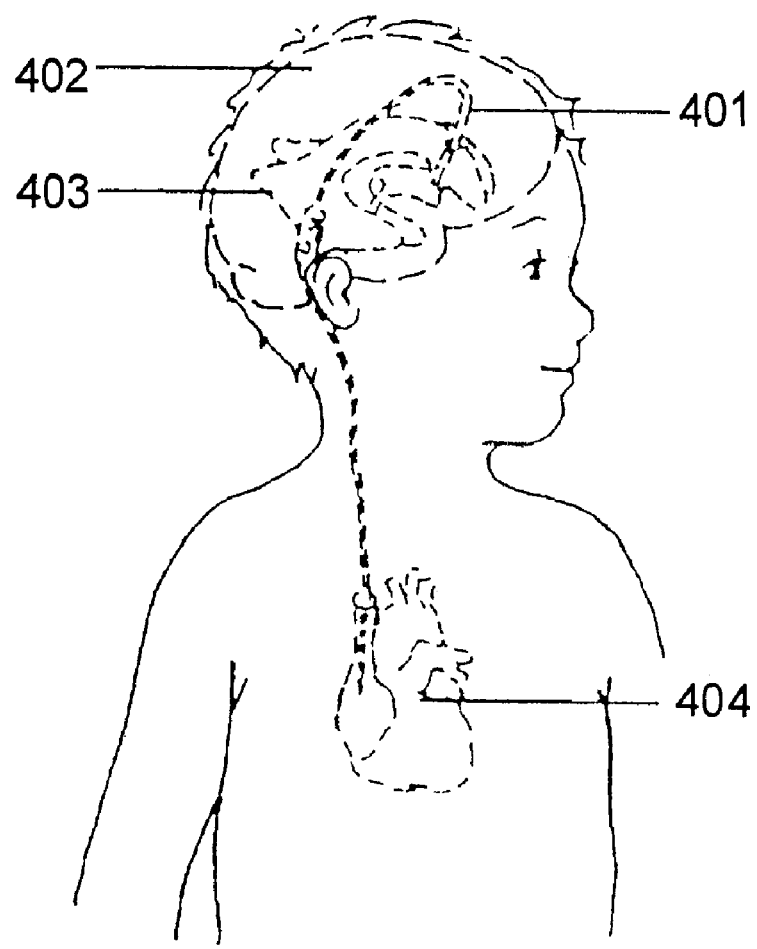
FIG. 1 shows an example of a hydrocephalus drainage arrangement connected to a patient.

FIG. 1 shows an example of a hydrocephalus drainage arrangement connected to a patient. The device comprises a ventriculo-atrial (VA) shunt 401. The VA shunt 401 moves cerebrospinal fluid from the ventricles 403, or spaces in the brain 402, into the atrium, or top chamber, of the heart 404 through a vein in the neck.

Figure 2:
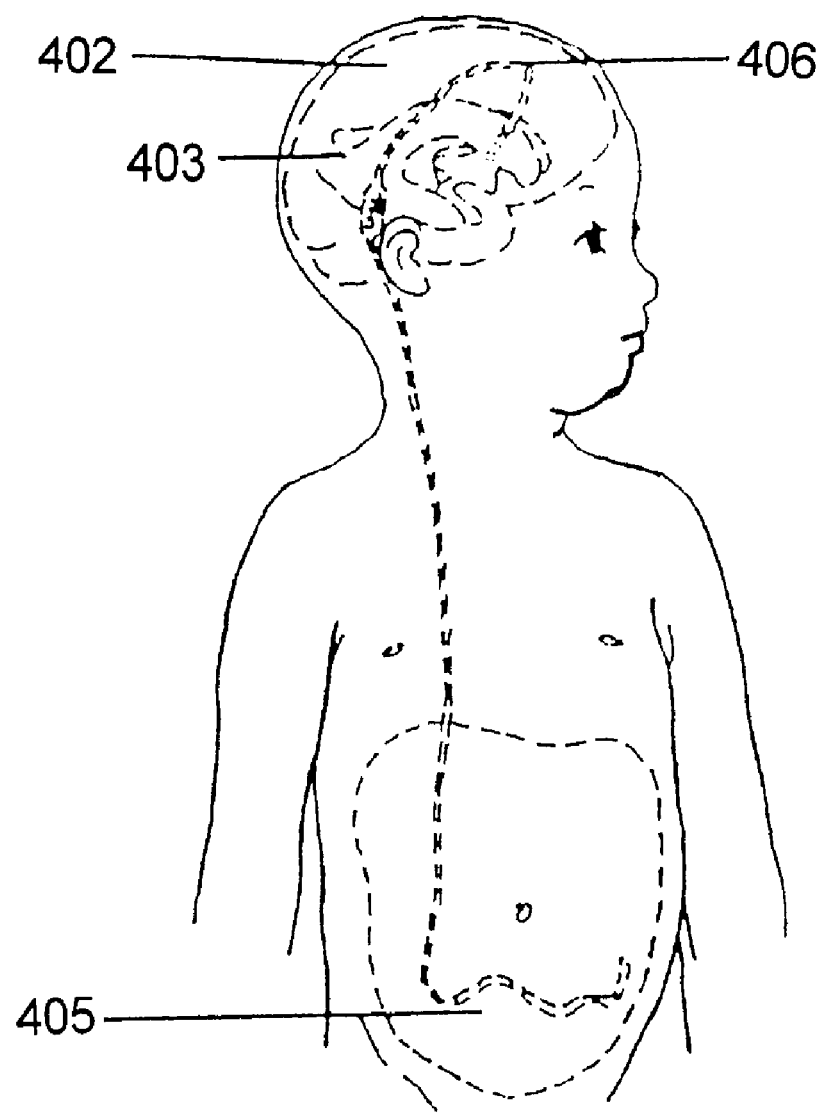
FIG. 2 shows another example of a hydrocephalus drainage arrangement connected to a patient.

FIG. 2 shows an example of a hydrocephalus drainage arrangement connected to a patient. The device comprises a ventriculo-peritoneal (VP) shunt 406. The VP shunt moves cerebrospinal fluid from the ventricles 403, or spaces in the brain 402, to a space in the peritoneal cavity inside the abdominal cavity 405. FIGS. 1 and 2 and the corresponding description are found in US20070093741, which is incorporated by reference herein.

Figure 3:
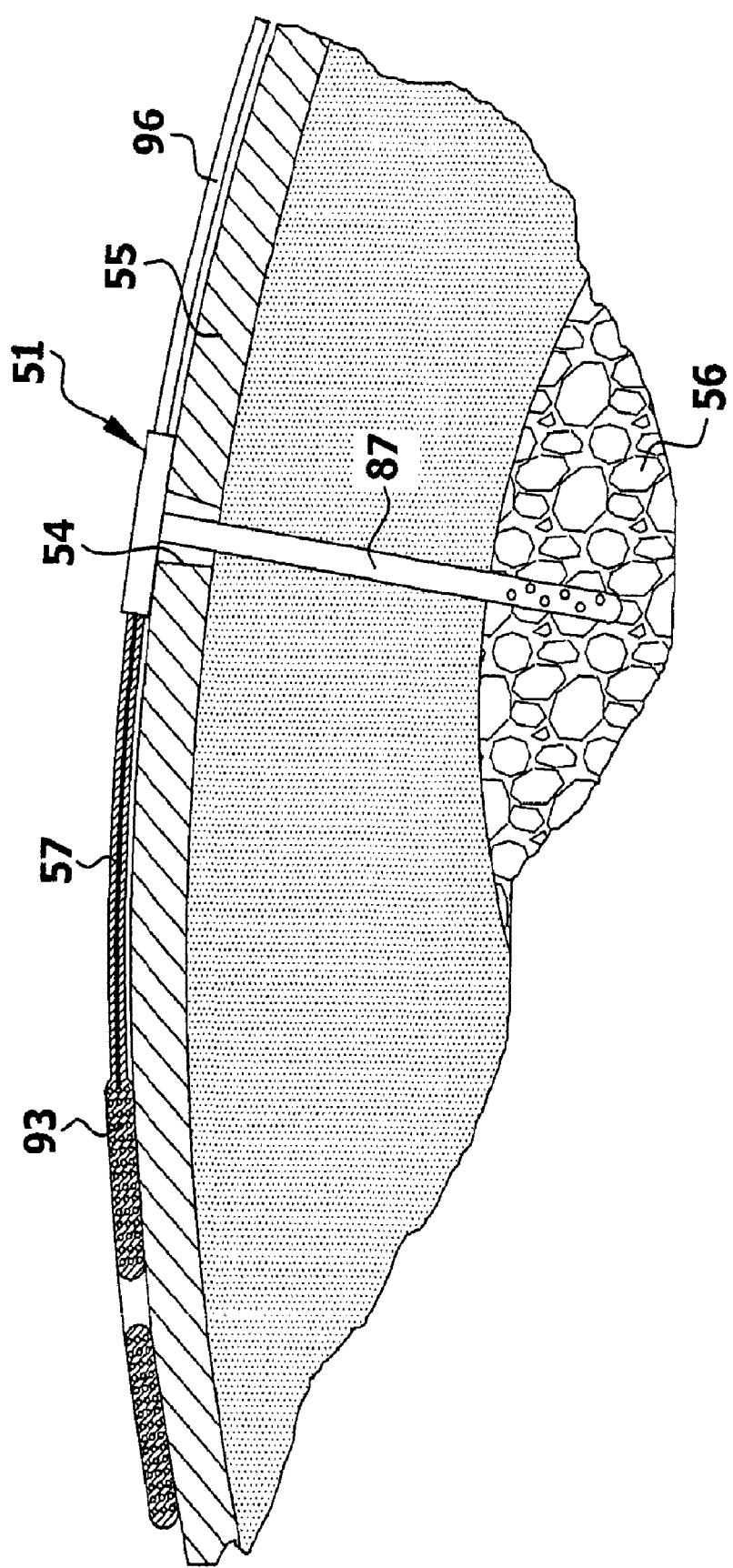
FIG. 3 shows an example of a hydrocephalus drainage device installed in a patient's cranium.
Figure 4:
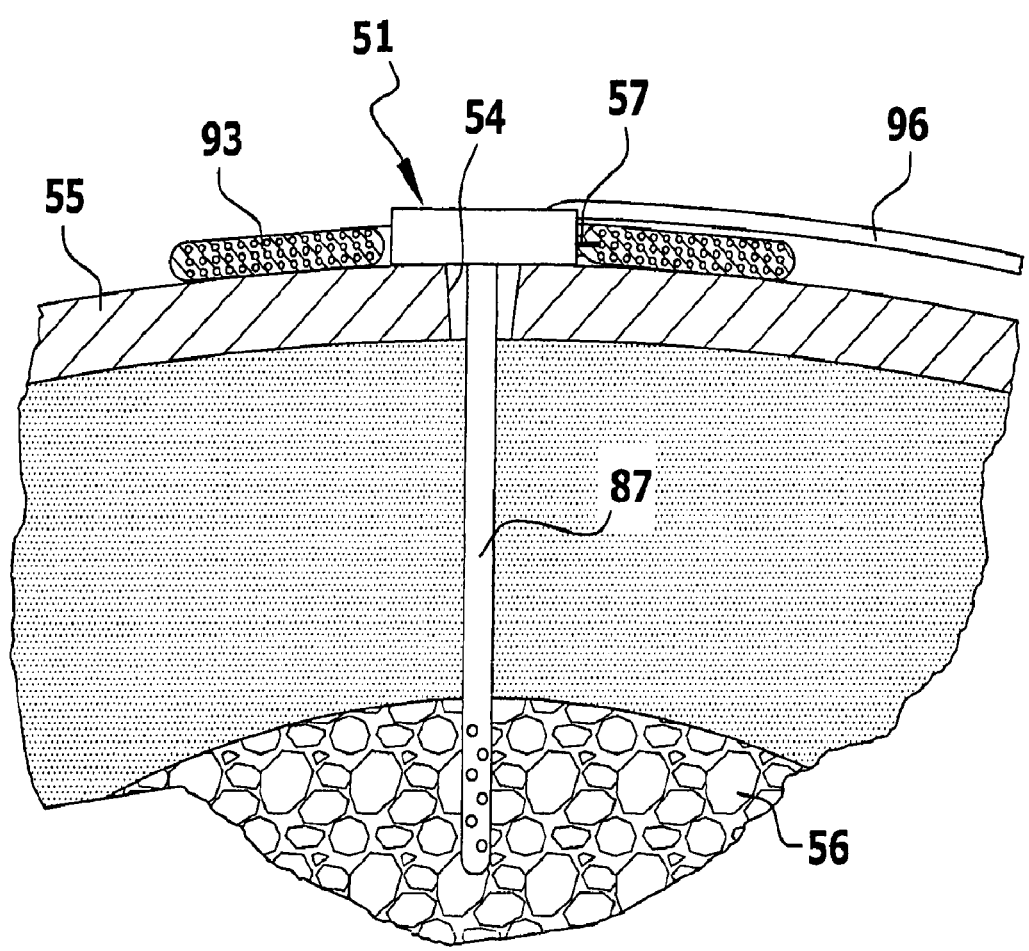
FIG. 4 shows the hydrocephalus drainage device of FIG. 3 installed in a patient's cranium.

FIGS. 3 and 4 show a housing 51 of a hydrocephalus drainage device placed in the brain 56 in this manner and a connection cable 57, which leads from the housing 51 onto the outside of the top of the cranium 55 and is connected to a coil, which is laid externally on the top of the cranium 55, i.e. between the top of the cranium 55 and the scalp, or in an alternative embodiment externally on the scalp. The described device is placed on the head in such a manner that the tube 87 is advanced at its free end in the manner of a catheter to the location of the brain, at which the intracranial pressure is to be measured. The housing 51 lies on the outside of the top of the cranium 55 with its floor surface, the pipe connection and the tube 87 then project through the drill hole 54 in the top of the cranium 55. The housing 51 thus serves as a drill hole covering. The housing 51 is arranged between the top of the cranium 55 and the scalp, a drainage pipe 96 can run directly on the top of the cranium 55 and under the scalp. A connection cable can lead directly to a coil 93, which is placed on the outside of the top of the cranium 55 outside the housing 51, i.e. either at a distance from the housing 51 next to this (FIG. 3) or to concentrically surround the housing 51 (FIG. 4). The device in FIGS. 3 and 4 is disclosed in U.S. Pat. No. 7,785,268, which is incorporated by reference herein.

Figure 5:
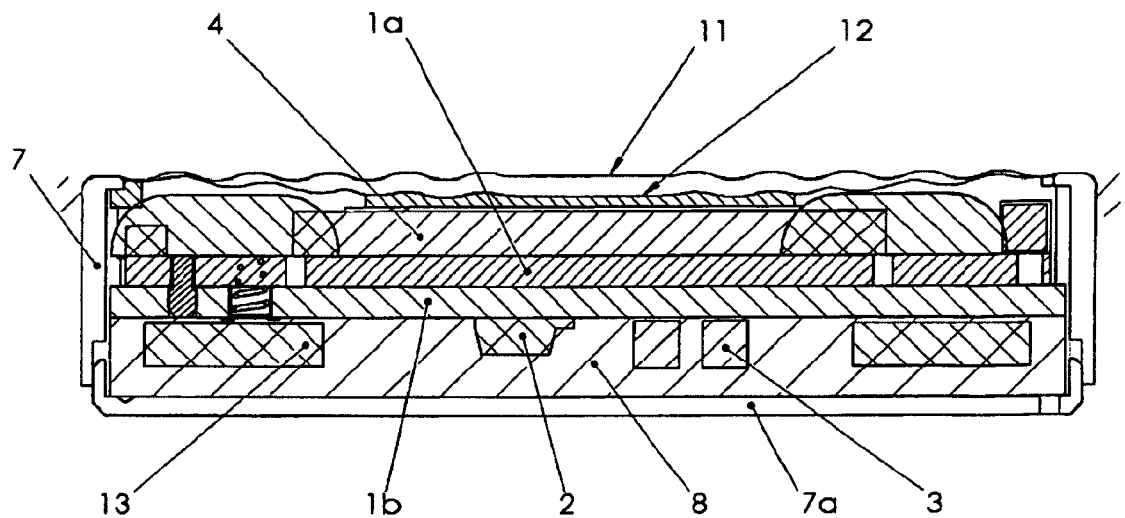
FIG. 5 shows the design of an intracranial pressure device with a turned part as the housing.

FIG. 5 shows the design of an intracranial pressure device with a turned part 7 of titanium as the housing. The parts are fixed into position in the housing 7 with a potting compound 8. The film 11 forms a membrane. Under the membrane is an air-filled cavity that is directly connected to the pressure sensor.

Quality assurance is made with the aid of a helium leak detector. The end of the housing 7 is sealed with a cap 7a and welded.

Figure 6:
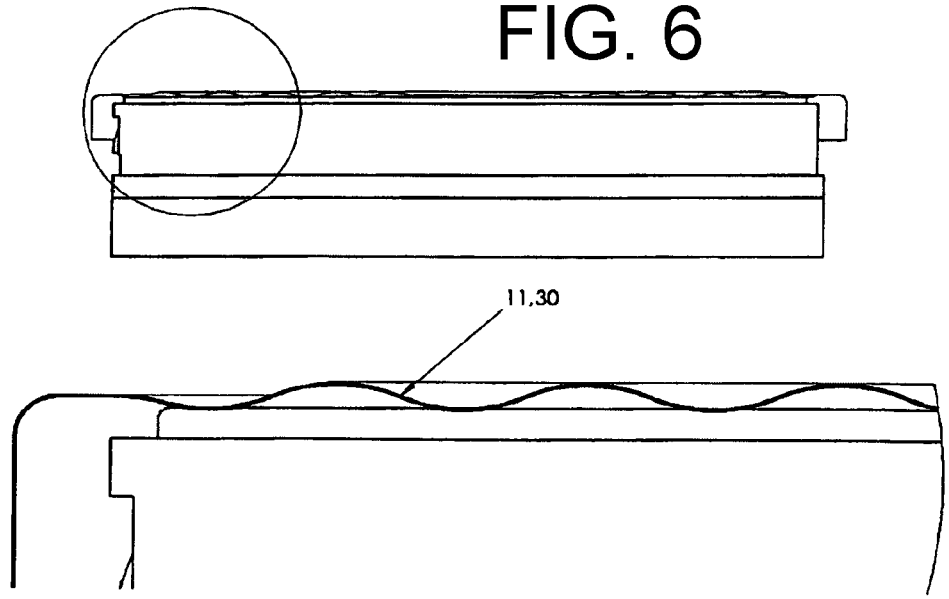
FIG. 6 shows a magnified single view of the area with the membrane.

FIG. 6 shows a magnified single view of the area with the membrane 11.

In contrast to known membranes, the membrane 11 is provided with corrugations 30. The corrugations 30 are circular in shape in the schematic illustration of FIG. 7. Here, a corrugation is connected up to the other. In the embodiment the corrugations 30 are sinusoidal. The amplitude of the sinusoidal corrugations in the embodiment is 0.8 millimeter. This 0.8 millimeter is disposed as ridges of 0.4 millimeter height and as furrows of 0.4 millimeter depth. The ridges from below are seen as vaults.

As a result of the corrugations 30, the membrane 11 is much more resilient than a flat membrane without corrugations.

Figure 8:
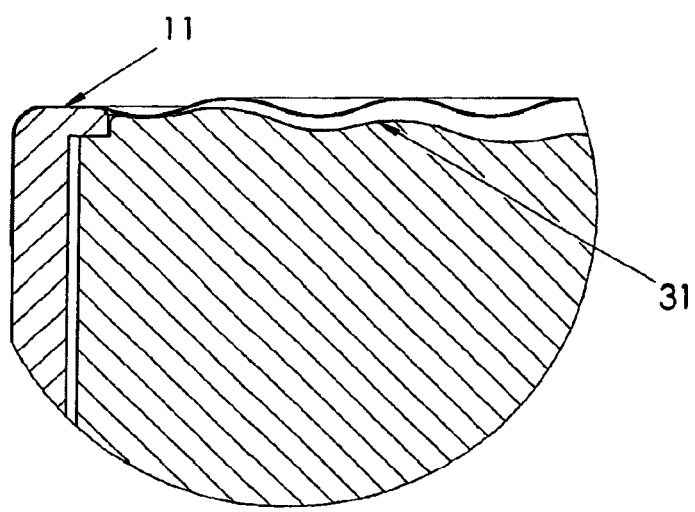
FIG. 8 shows another possible embodiment of the present application where the membrane contact surface of the intracranial pressure device is matched to the profile given by deforming the membrane.

In another embodiment according to FIG. 8, the membrane contact surface 31 of the measurement device is matched to the profile given by deforming the membrane, such that the downward facing furrows of the corrugation 30 lay in the indentations in the membrane contact surface 31 and the ridges of the membrane contact surface 31 lay in the vaults of the corrugations 30. In this way, subsequent to a membrane deformation, the volume present between the membrane 11 and the membrane contact surface 31 is significantly reduced.

Figure 9:
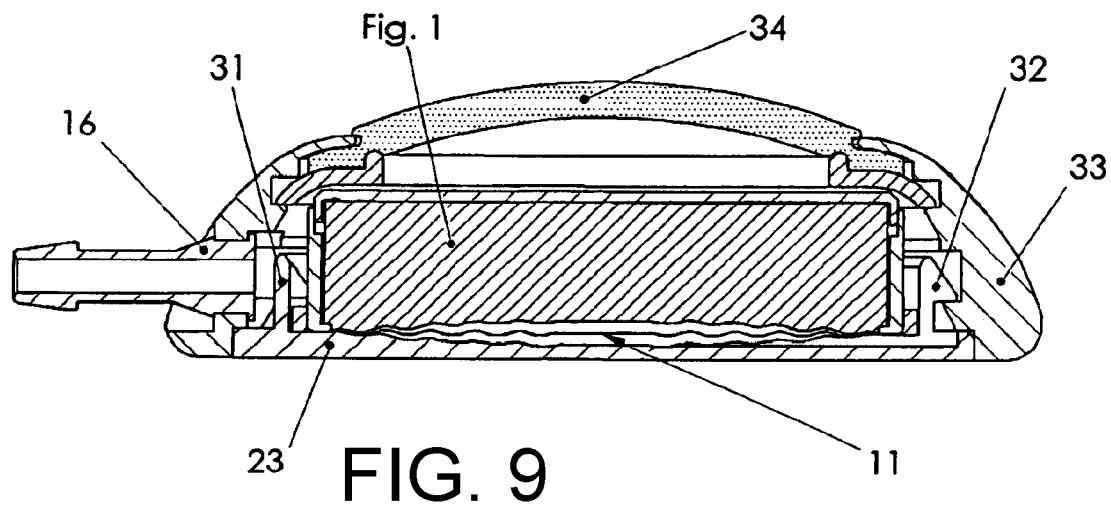
FIG. 9 shows an outline display of the intracranial pressure device on a drainage line according to one possible embodiment.

The measuring device according to the present application is also suitable, inter alia, for recording the liquid pressure in a drainage line for liquor in a shunt system for the treatment of hydrocephalus. FIG. 9 shows in one possible embodiment an outline display of such a measuring device on a drainage line 16.

The measuring device includes a reservoir housing and a measuring cell as described in FIG. 5 with titanium membrane 11.

Figure 7:
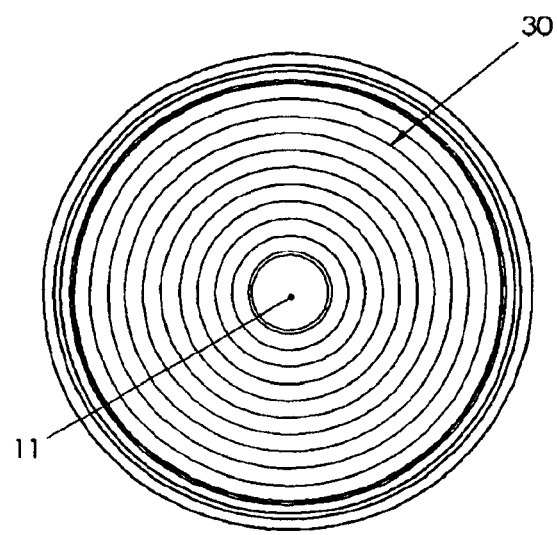
FIG. 7 is a schematic illustration of corrugations.

The above parts cooperate as in the measuring device according to FIGS. 5 to 7. The embodiment of FIG. 5 differs by the additional external housing that protects the titanium membrane 11 by negative pressure and enables a pressure measurement in the closed shunt system.

The reservoir housing in the possible embodiment as shown in FIG. 9 comprises essentially a rotatory main body 33, the floor 23 with the corrugated opposite side to the membrane 11 and the cover 34. The outlet occurs through the nozzle 16.

The floor 23 possesses a number of snap-in hooks 31/32, for which corresponding grooves are provided in the main body as well as in the housing of the measuring cell. The floor in one possible embodiment possesses three hooks that are offset at 120 degrees to each other on the periphery. Other dispositions or additional snap-in hooks are possible. The snap-in hooks 31 for the assembly of the measuring cell point inwards, the snap-in hooks 32 for the main body point outwards. For the assembly, the measuring cell is positioned into the floor 23 such that the inner snap-in hooks 31 of the floor snap into the grooves of the measuring cell. The floor 23 with the measuring cell is then pressed into the main body 33 until the snap-in hooks snap into the grooves provided for them in the main body. The cover 34 is thus fixed in its position. This form-fitting positioning is free of play by means of an appropriate construction of the hooks and grooves. The assembly of the housing is irreversible, once assembled the whole module cannot be disassembled without breaking it. This significantly increases the security of the product, as an improper use of the disassembled end product is excluded.

According to the present application, the implantable device for recording intracranial pressures comprises a pressure measuring unit in the form of a microchip and a corrugated, biocompatible membrane for transferring pressure from outside to the interior, wherein on the sensor side the pressure is further transferred through an extremely small chamber filled with air or a gas.

As seen in FIG. 5, there is a microchip 4 with pressure sensor technology, two separate circuit boards 1a and 1b and additional electronic components 2, 3. The electronic components are positioned on the circuit board 1, the measurement signal is sent by a sensor coil 13 to an externally placed receiving unit. The measuring device measures changes in brain liquor pressure on the membrane which are passed on through the air column in the cavity 12 to the pressure sensor. This produces electric signals that are transmitted telemetrically to an externally located receiver.

Figure 10:
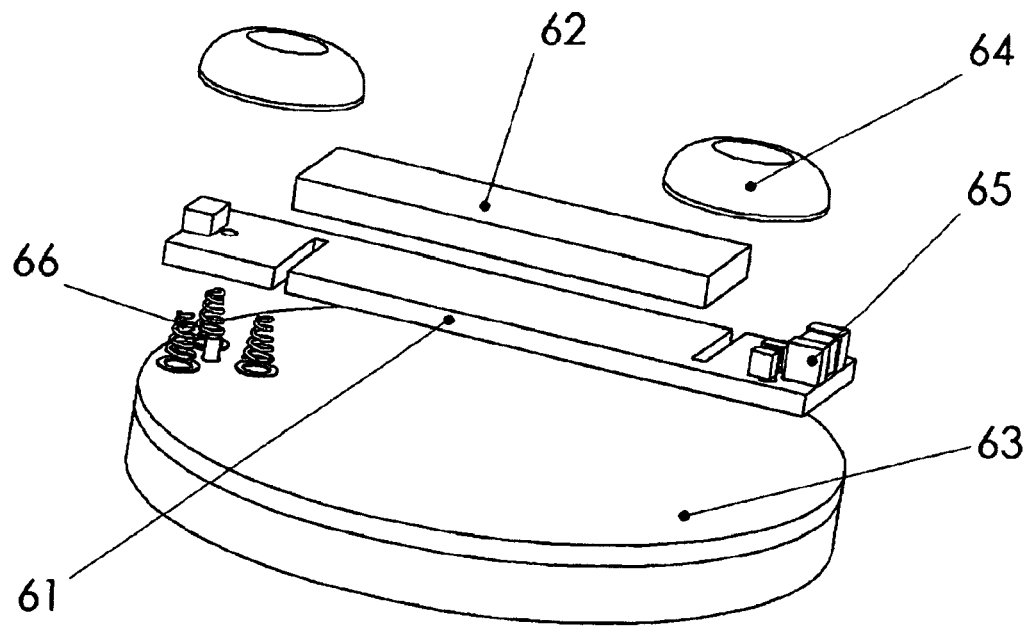
FIG. 10 shows an exploded view of a portion of an intracranial pressure device according to one possible embodiment.

FIG. 10 shows an exploded view of the design of the base board 61 of the ASIC sensor chip 62 and the assembly of the circuit board on the main board 63. The base board 61 is slotted to offset any mechanical effect on the chip 62. The chip is adhesively bonded centrally at one point to the circuit board 61. The contacts are bonded (not shown), the connections are each protected by a Glop Top 64. Various capacitors 65 are located on the base board 61 to regulate the voltage of the ASIC chip 62. The base board 61 is connected to the main board 63 through spiral spring-like contact wires 66.

Figure 11:
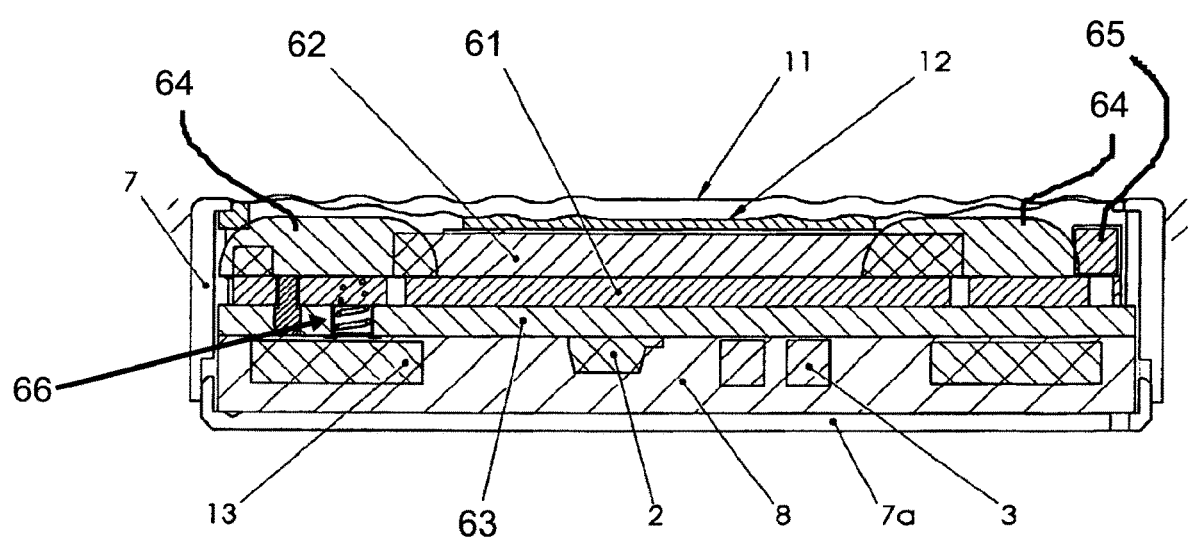
FIG. 11 shows another possible embodiment of the design of the intracranial pressure device with a turned part as the housing.

FIG. 11 shows one possible embodiment of a pressure sensor according to the present application. As shown in FIG. 5, the pressure sensor may comprise a housing 7, electronic components 2 and 3, a potting compound 8, a membrane 11, a cavity 12, and a sensor coil 13. As shown in FIG. 10, the pressure sensor may also comprise a base board 61, a sensor chip 62, a main board 63, glop tops or glob tops 64, capacitors 65, and contact wires or contacts 66.

The present application intends to create a pressure gage that offers a static and dynamic operation, in one possible embodiment in regard to a long-term, drift-free operation of the implanted sensor. The appliance should be integrated in an existing shunt system employed for the treatment of hydrocephalus. The appliance should address deficiencies in prior art pressure sensors and components and methods of use, as in the following discussion of prior art devices.

Further examples of hydrocephalus treatment technology are disclosed in different published patents and patent applications. An implantable pressure sensor, described in patent DE 196 38 813 C1, is connected with flexible printed circuits and is enclosed in the area of the sensor element by a substrate that has a higher mechanical strength than the printed circuit and together with the sensor element is embedded into a flexible compound. The design is intended to make possible a reliable and cost-efficient measurement device that, however, due to the passage through the skin, does not offer any reduction in the risk of infection. In connection with the sensor technology, reference is made to U.S. Pat. No. 4,738,267, in which a plastic capsule with membrane is used, onto which a strain gage is applied. The deflection of the Wheatstone bridge is interpreted as the amount of applied pressure. A sensor of this type is inaccurate and has an unacceptably high drift behavior. For this reason it has not gained acceptance as an implantable intracranial pressure sensor.

As a continuation of the application DE 196 38 813 C1, the application DE 197 05 474 also describes the analogous technology for telemetrically collecting intracorporeal pressures. However, no indication was given on how the biocompatibility should be essentially ensured and/or promoted. A sensor of this type is not yet ready to enter the market.

Another method for reading the intracranial pressure is described in U.S. Pat. No. 6,113,553. Here, the filed claims, by describing the electronic design, relate to a long-term measurement that is as drift-free as possible. A capacitive design is used here, wherein the sensor is intended to be countersunk in the bone. This may be necessary and/or desired due to the bulky design of the sensor. In how far the actual properties of the sensor concept satisfy the strict requirements of the intracranial pressure measurement in terms of accuracy and drift behavior is not known, as a sensor of this type is not yet available on the market and consequently has not been able to be subjected to independent testing.

A method for recording the intracranial pressure without piercing the skin is likewise described in the 1987 U.S. Pat. No. 4,676,255. A sensor located under the skin is at its zero position as long as intracranially no positive or negative differential pressure exists towards the surroundings. If the intracranial pressure rises or falls then the sensor is moved from its zero position. The amount of pressure that may be needed and/or desired to return the sensor to its zero position is then applied externally through the skin. The pressure that may be required and/or desired for this should then correspond to the intracranial pressure. This method was not able to become clinically accepted. The reasons for this are the variations of the skin from patient to patient, the technically difficult and inaccurate determination of the zero point as well as the complicated fabrication of the required and/or desired external pressure pad.

In the Patent DE 198 58 172 a method is described that directly records the intracorporeal pressure by means of a sensor element based on microsystem technology. The focus of attention concerns the recording of the internal pressure of the eye. The implant should therefore be as small and as light as possible. When using this technology for recording the intracranial pressure, the coating of the sensor is of critical importance. In the Patent DE 101 56 494 there is described a sensor of this type, in which a metallic layer as well as at least sections of a biocompatible plastic layer are provided in order to essentially ensure and/or promote the biocompatibility. A design of this type has considerable disadvantages. Such a coating of the sensor element allows the measurement to be impaired because of the transit through this layer, whose properties can change in the course of time. The layer can be damaged due to externally acting forces. The drift behavior is problematic at least due to aging, for example of the plastic layers.

In Patent EP 1 312 302 A2 a technique is described, in which a medium arranged around the sensor is enclosed by a flexible shell. In the publication no description is made of how the biocompatibility of the flexible shell should be essentially ensured and/or promoted. In the application, the favored use of silicone oil for the optimal transfer of the applied pressure seems, in the light of a risk assessment, to be problematic.

Another device described in EP 1 312 302 is composed of the following features: a) intracorporeal intracranial pressure measurement; b) with an implantable measuring device; c) with a sensor element; d) with a telemetric unit, comprising an inductive coil; e) with a support, in or on which the sensor element and the telemetric unit are located; f) with a flexible encasement of support, telemetric unit and sensor element; g) with a connectable extracorporeal analysis system; and h) a connectable telemetric retrieval/scanning device.

In this regard it should be noted that EP 1 312 302 aims essentially to use a liquid as the pressure transfer medium, although the possibility of using gas as the pressure transfer medium is also mentioned in EP 1 312 302. For the person skilled in the art, the liquid as the pressure transfer medium has the attraction of being practically uncompressible. Thus, pressure changes are immediately and/or substantially immediately transmitted without modification. The preference for liquid pressure agents is unmistakable.

U.S. Pat. No. 6,673,022 B1 likewise discloses an implantable device for the intracranial pressure measurement. U.S. Pat. No. 6,673,022 refers to a bladder made of soft material on the end of a catheter shaped device. In the operational state the soft material is uncontrollably deformed, such that the reliability of the measurement is questionable.

In the known device, the measuring unit is seated on the end of the device opposite to the tip. The bladder encloses a volume of air.

DE102005020569 also stems from an implantable measuring unit that comprises a sensor, wherein the measuring unit is provided with a flexible encasement and comprises a pressure transducer and wherein the pressure transducer (optionally together with the telemetric electronics) is arranged in a chip and embedded in a pressure medium, wherein the encasement encloses the pressure medium. The term that is used here "embedding/encasing" also includes a force/impingement on part of the surface of the pressure transducer with the pressure medium.

DE 102005020569 forms the basis for WO2006/11712. Hereinafter, when DE102005020569 is mentioned, it also includes WO2006/11712.

DE102000520569 describes a small-volume encasement of an implantable measuring unit, wherein the measuring unit is embedded in liquid or gas, for example with data transmission, for example with a metallic housing and a window for a transfer of pressure onto the measuring unit, wherein the window is sealed with a membrane, in one possible embodiment with a metallic membrane. In this regard, a miniaturized chip for recording the pressure should be placed into a housing, in such a manner that firstly essentially ensures and/or promotes also the long term biocompatibility of the implant and secondly that a highly accurate measurement can be made that is as drift free as possible. In this regard, DE102005020569 is intended to overcome the difficulties with the passivation of the electronically working sensor which are observed for example in the reliability of the protection in regard to aging or damage, in the impairment of the pressure transfer through the deposited protective layer and in the incalculable drift that results from the effect of material changes over time.

In order to overcome these problems DE102005020569 proposes to incorporate the sensor into a metallic housing, in one possible embodiment made of titanium. The external pressure on the housing is transferred onto the inside of the sensor through a leak-proof, biocompatible membrane that is as elastic as possible and mounted above the sensor. Similarly, the membrane in one possible embodiment of the present application comprises titanium. However, other membranes can also be considered.

In spite of the technical feasibility of the present application according to DE102005020569, up to now a corresponding commercially acceptable product could not be developed. The reasons for this are firstly the economic and technical constraints, the somewhat costly fabrication leading to high manufacturing costs.

In DE10239743 as well as in this context DE102005008454 and DE102008011601 there is described an implantable sensor that carries a miniaturized sensor chip on the tip of a catheter to measure pressure and temperature. Here, electronic modules for evaluating the sensor technology, for the telemetric transmission as well as the energy supply are mounted on a circuit board. This circuit board is encapsulated in a housing made of implantable material. The sensor can be very small when it is separated from the electronics. Here, the body assembly is located in a ceramic housing that is implanted under the skin, a thin catheter carries a pressure sensor in the tip. The catheter is made of an elastomeric material. The sensor is sealed in a hardening material. However, a sensor with this design is able up to now to supply a usable signal for relatively short periods, because due inter alia to aging and water uptake of the plastic, the values drift. Attenuating the encapsulation material has a deleterious effect on the dynamic behavior, thereby making difficult the measurement of impulse waves. The design is barely suitable for negative pressures, as the tensile loads are not transmitted well enough by the encapsulation material. The product can be implanted for short periods, approved for 28 days, and the integration into an existing shunt system is not possible.

Some examples of corrugated membranes may be found in the following publications: DE102007056844, DE102007024270, DE102008037736, DE102008033337.

DE102007056844 relates to a pressure transducer. The pressure transducer comprises a diaphragm seal, as well as a pressure sensor with a pressure sensitive, elastic deformation element and a transducer element for emitting an electric or optical signal that depends on a deformation of the deformation element, wherein the pressure chamber is hydraulically connected to the deformation element of the pressure sensor over a hydraulic path that includes a line filled with a transfer fluid. The deformation element is optionally designed as a corrugated membrane. DE102007056844 covers in detail the production of a membrane bed, on which the membrane under corresponding pressure can come into contact. The membrane bed should comprise an imprint of the membrane, wherein the imprint is produced by electrical discharge machining (EDM).

DE102007056844 also deals with radial breaks of the corrugations of the membrane bed.

DE102007056844 does not comprise any indication on the dimensions of the corrugations or of the membrane and on the application for measuring intracranial pressure.

DE102008037736 also has a corrugated membrane that is associated with a similarly corrugated contact surface. The membrane, like the membrane of DE102007056844, should withstand pressures. In this publication there is also no indication of the dimensions of the corrugations and of the application for measuring intracranial pressures. In addition the membrane has a hub that can be utilized as a drive unit for a control or the like. In contrast, the membrane movements produced with the device are not suitable as a drive unit.

DE102007024270 also has a corrugated membrane that is associated with a similarly corrugated contact surface. A special feature is disclosed in DE102007024270 in that the edge region directly adjacent to the attachment surface of the membrane opposite to the membrane bed runs at a distance. An indication to the dimensions of the membrane and to its application for measuring intracranial pressure is also not found in the publication.

DE102008033337 continues on from the disclosure DE102007056844 and comprises various proposals for taking into account an unsymmetrical membrane deformation. The unsymmetrical membrane deformation results from a curved membrane that extends over a recessed membrane bed and is irrelevant for the membrane and its deformation.

One feature or aspect of an embodiment is believed at the time of the filing of this patent application to possibly reside broadly in an implantable device for recording intracranial pressures, wherein a pressure sensor is used that interfaces with a data transmitter, and wherein the pressure sensor is a microchip and the microchip is located in a rigid housing, wherein a window is provided in the housing for transferring the pressure and the window is sealed with a thin membrane, wherein the membrane is in one possible embodiment made of a biocompatible metal, and wherein the membrane acts on a volume of fluid, in one possible embodiment on a volume of gas as the pressure mediator that transfers the pressure changes on the membrane to the pressure sensor, wherein the membrane possesses at least one corrugation wherein the corrugation has at least one outward bulge with a radius that is at least equal to a multiple of the thickness of the membrane, in one possible embodiment at least equal to ten times the thickness of the membrane and another possible embodiment at least equal to fifty times the thickness of the membrane and in yet another possible embodiment at least equal to one hundred times the thickness of the membrane, wherein the membrane thickness is in one possible embodiment 0.005 to 0.04 millimeter, in another possible embodiment 0.01 to 0.03 millimeter.

Another feature or aspect of an embodiment is believed at the time of the filing of this patent application to possibly reside broadly in the device, wherein the corrugations form a plurality of outward bulges that face upwards and/or downwards.

Yet another feature or aspect of an embodiment is believed at the time of the filing of this patent application to possibly reside broadly in the device, wherein the membrane is corrugated on at least one-third of the pressure-impinged surface, in one possible embodiment on at least two-thirds of the pressure-impinged surface and in yet another possible embodiment on at least four-fifths of the pressure-impinged surface.

Still another feature or aspect of an embodiment is believed at the time of the filing of this patent application to possibly reside broadly in the device, wherein the corrugation runs annularly.

A further feature or aspect of an embodiment is believed at the time of the filing of this patent application to possibly reside broadly in the device, wherein a plurality of corrugations of different diameter are arranged concentrically.

Another feature or aspect of an embodiment is believed at the time of the filing of this patent application to possibly reside broadly in the device, wherein the concentrically arranged corrugations at least partly merge into one another.

Yet another feature or aspect of an embodiment is believed at the time of the filing of this patent application to possibly reside broadly in the device, wherein a membrane contact surface faces the membrane.

Still another feature or aspect of an embodiment is believed at the time of the filing of this patent application to possibly reside broadly in the device, wherein the membrane contact surface is
a) at least partly flat and/or
b) at least partly curved and/or
c) is least partly funnel-shaped and/or
d) at least partly hill-shaped.

A further feature or aspect of an embodiment is believed at the time of the filing of this patent application to possibly reside broadly in the device, wherein the membrane contact surface is also corrugated, such that the membrane with its bulges that face toward the membrane contact surface can lay in the latter's recesses and the membrane contact surface for its part can lay with the bulges that face towards the membrane in the membrane's inward bulges.

Another feature or aspect of an embodiment is believed at the time of the filing of this patent application to possibly reside broadly in the device, wherein on using a volume of gas as the pressure mediator between membrane and pressure sensor, the membrane possesses an active swept volume that is greater than the gas volume that exists between the membrane and the pressure sensor after maximum deformation of the membrane.

Yet another feature or aspect of an embodiment is believed at the time of the filing of this patent application to possibly reside broadly in the device, wherein the active swept volume is at most four times greater, in one possible embodiment at most two times greater than the passive part of the chamber volume, wherein the passive part of the chamber volume is the volume of gas that exists between the membrane and the pressure sensor after maximum deformation of the membrane.

Still another feature or aspect of an embodiment is believed at the time of the filing of this patent application to possibly reside broadly in the device, wherein for a circular membrane, the maximum radius of the membrane is at least fifteen times, in one possible embodiment at most fifty times greater than the maximum membrane stroke.

A further feature or aspect of an embodiment is believed at the time of the filing of this patent application to possibly reside broadly in the device, wherein the chamber volume, comprising the active and passive volume, is between twenty cubic millimeters and at most three hundred fifty cubic millimeters, in one possible embodiment at most on hundred thirty cubic millimeters.

One feature or aspect of an embodiment is believed at the time of the filing of this patent application to possibly reside broadly in the device, wherein the membrane is in a pressure range of eight hundred to one thousand two hundred millibar without touching the membrane contact surface.

Another feature or aspect of an embodiment is believed at the time of the filing of this patent application to possibly reside broadly in a method for manufacturing the device, wherein when a metallic membrane is used, the membrane for corrugation is deep drawn when cold past the elastic yield point.

Yet another feature or aspect of an embodiment is believed at the time of the filing of this patent application to possibly reside broadly in the method, wherein for the formation of the corrugations the membrane is shaped on a mold surface that is a copy of the corrugation, wherein the contours of the mold surface are deepened until the desired corrugation is achieved on the membrane.

Still another feature or aspect of an embodiment is believed at the time of the filing of this patent application to possibly reside broadly in the method, wherein the membrane contact surface is copied from the shaped membrane.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

A Glop Top or Glob Top may be a compound or epoxy may encapsulate a semiconductor chip, wire bond, connection, and/or contact, in order to protect against moisture, chemicals, and contaminants. One example of a Glop Top or Glob Top epoxy may be manufactured by Master Bond Inc., headquartered at 154 Hobart Street, Hackensack, N.J. 07601.

U.S. patent application Ser. No. 12/981,224, filed on Dec. 29, 2010, having inventor Christoph MIETHKE, and title "CEREBROSPINAL FLUID DRAINAGE", having Publication No. US 2011-0166495 A1, and its corresponding Federal Republic of Germany Patent Application No. 10 2008 030 942, filed on Jan. 7, 2010, and International Patent Application No. PCT/EP2009/004751, filed on Jul. 1, 2009, having WIPO Publication No. WO 2010/000461 and inventor Christoph MIETHKE are hereby incorporated by reference as if set forth in their entirety herein.

U.S. patent application Ser. No. 13/478,157, filed on May 23, 2012, having inventor Christoph MIETHKE, and title "IMPLANTABLE HYDROCEPHALUS SHUNT SYSTEM", having Publication No. US 2012-0232462 A1, and its corresponding Federal Republic of Germany Patent Application No. 10 2009 060 533.9, filed on Dec. 23, 2009, and International Patent Application No. PCT/EP2010/007817, filed on Dec. 21, 2010, having WIPO Publication No. WO 2011/076382 and inventor Christoph MIETHKE are hereby incorporated by reference as if set forth in their entirety herein.

U.S. patent application Ser. No. 11/149,928, filed on Jun. 10, 2005, having inventor Christoph MIETHKE, and title "METHOD OF TREATING A PATIENT WITH HYDROCEPHALUS AND APPARATUS THEREFOR", having Publication No. US 2007-0004999 A1, and its corresponding U.S. Pat. No. 7,422,566, issued on Sep. 9, 2008, and its corresponding Federal Republic of Germany Patent Application No. 103 47 278.9, filed on Oct. 8, 2003, and Federal Republic of Germany Patent Application No. 102 58 070.7, filed on Dec. 11, 2002, and International Patent Application No. PCT/EP03/13999, filed on Dec. 10, 2003, having WIPO Publication No. WO 2005/092424 and inventor Christoph MIETHKE are hereby incorporated by reference as if set forth in their entirety herein.

U.S. patent application Ser. No. 11/535,242, filed on Sep. 26, 2006, having inventor Christoph MIETHKE, and title "ADJUSTABLE HYDROCEPHALUS VALVE", having Publication No. US 2007-0093741 A1, and its corresponding U.S. Pat. No. 7,766,855, issued on Aug. 3, 2010, and its corresponding Federal Republic of Germany Patent Application No. 10 2004 015 500.3, filed on Mar. 27, 2004, and International Patent Application No. PCT/EP05/03052, filed on Mar. 22, 2005, having WIPO Publication No. WO 2004/052443 and WIPO Publication No. 2005/092424 and inventor Christoph MIETHKE are hereby incorporated by reference as if set forth in their entirety herein.

All of the following patents, patent applications, patent publications, and other documents, except for the exceptions indicated herein, are hereby incorporated by reference as if set forth in their entirety herein except for the exceptions indicated herein, as follows: WO 2006/117123, having the title "IMPLANTABLE DEVICE FOR RECORDING INTRACRANIAL PRESSURES," published on Nov. 9, 2006; DE 10 2007 056844, having the English translation of German title "Membrane bed for pressure transmission device of e.g. differential pressure transducer, has surface with spiral outline that serves as embossing pattern for flexible metallic and embossed membranes, where outline is obtained by die sinking," published on Jun. 10, 2009; DE 10 2007 008642, having the German title "Messeinrichtung für physiologische Parameter," published on Aug. 14, 2008; DE 10 2008 033337, having the German title "Druckmittler and Druckmessgerät mit einem solchen Druckmittler," published on Jan. 21, 2010; DE 10 2008 037736, having the English translation of the German title "Pressures and/or pressure changes detecting device e.g. high pressure-resistant control element, has base part forming boundary for deformation of membrane, where membrane is provided with corrugated profile," published on Feb. 18, 2010; and DE 10 2007 024270, having the English translation of the German title "Diaphragm for pressure transmitter, has concentrically arranged outer edge region that is provided directly adjacent to attachment surface, where edge region runs at distance opposite to diaphragm bed and/or diaphragm bed body," published on Nov. 27, 2008.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of draining cerebrospinal fluid in a patient having hydrocephalus using a hydrocephalus shunt arrangement, said method comprising the steps of:

inserting a ventricle catheter of said hydrocephalus shunt arrangement into a ventricle space of the brain within the cranium of a patient having excess cerebrospinal fluid in the ventricle space;

connecting said ventricle catheter to a first cerebrospinal fluid drainage line of said hydrocephalus shunt arrangement;

connecting said first cerebrospinal fluid drainage line to a control valve of said hydrocephalus shunt arrangement, which control valve is configured to control the drainage of cerebrospinal fluid from the cranium of the patient;

connecting said control valve to a second cerebrospinal fluid drainage line of said hydrocephalus shunt arrangement;

inserting an open end of said second cerebrospinal fluid drainage line to a drainage area comprising a peritoneal cavity inside an abdominal cavity of the patient;

implanting an intracranial device under the skin of the patient in or at the cranium of the patient and connecting said intracranial device to said ventricle catheter or said control valve, which said intracranial device comprises
   a chamber formed within a rigid housing by
      a corrugated metal membrane with alternating bulges, which project outwardly, and indentations, which project inwardly, said membrane being disposed to cover an opening of said rigid housing, and
      a corrugated wall with alternating bulges, which project outwardly, and indentations, which project inwardly, disposed opposite said membrane,
   wherein each of said membrane and said corrugated wall comprises a similar cross-sectional profile of similar bulges and indentations such that, upon movement of said membrane toward said wall, at least one of said bulges of said membrane contacts and covers a corresponding one of said bulges of said wall, and
   wherein said chamber contains a pressure medium therein to transfer intracranial pressure from said membrane, which is configured to move upon a change in intracranial pressure, to a pressure device of said intracranial device;

transferring intracranial pressure from said membrane to said pressure device of said intracranial device;

setting said drainage control valve to produce a desired, controlled, drainage of excess cerebrospinal fluid from the cranium of the patient; and draining excess cerebrospinal fluid from the ventricle inside the cranium of the patient and into the peritoneal cavity inside the abdominal cavity of the patient.

2. The method according to claim 1, wherein:
said wall comprises a cross-section that is flat or curved or funnel-shaped.

3. The method according to claim 1, wherein:
said wall comprises a concave or funnel-shaped cross-section; and
said membrane is disposed to cover said wall such that, upon movement of said membrane toward said wall, contact between said membrane and said wall proceeds from a perimeter edge to a central portion of said wall.

4. A hydrocephalus shunt arrangement for draining cerebrospinal fluid in a patient having hydrocephalus, said hydrocephalus shunt arrangement comprising:
a ventricle catheter being configured to be inserted into a ventricle space of the brain within the cranium of a patient having excess cerebrospinal fluid in the ventricle space;

a first cerebrospinal fluid drainage line being connected to said ventricle catheter;

a control valve being connected to said first cerebrospinal fluid drainage line, which control valve being configured to control the drainage of cerebrospinal fluid from the cranium of the patient;

a second cerebrospinal fluid drainage line being connected to said control valve;

said second cerebrospinal fluid drainage line being configured to be inserted into a drainage area comprising a peritoneal cavity inside an abdominal cavity of the patient;

an intracranial device being configured to be implanted under the skin of the patient in or at the cranium of the patient and being connected to said ventricle catheter or said control valve, which said intracranial device comprises
   a chamber formed within a rigid housing by
      a corrugated metal membrane with alternating bulges, which project outwardly, and indentations, which project inwardly, said membrane being disposed to cover an opening of said rigid housing, and
      a corrugated wall with alternating bulges, which project outwardly, and indentations, which project inwardly, disposed opposite said membrane,
   wherein each of said membrane and said corrugated wall comprises a similar cross-sectional profile of similar bulges and indentations such that, upon movement of said membrane toward said wall, at least one of said bulges of said membrane contacts and covers a corresponding one of said bulges of said wall, and
   wherein said chamber contains a pressure medium therein to transfer intracranial pressure from said membrane, which is configured to move upon a change in intracranial pressure, to a pressure device of said intracranial device; and said control valve being configured to be set to produce a desired, controlled, drainage of excess cerebrospinal fluid from the ventricle inside the cranium of the patient and into the peritoneal cavity inside the abdominal cavity of the patient.

5. The hydrocephalus shunt arrangement according to claim 4, wherein:
said wall comprises a cross-section that is flat or curved or funnel-shaped.

6. The hydrocephalus shunt arrangement according to claim 4, wherein:
said wall comprises a concave or funnel-shaped cross-section; and
said membrane is disposed to cover said wall such that, upon movement of said membrane toward said wall, contact between said membrane and said wall proceeds from a perimeter edge to a central portion of said wall.

7. The hydrocephalus shunt arrangement according to claim 6, wherein:
said membrane has a thickness in a range of 0.005 millimeters to 0.04 millimeters; and
at least one of said bulges having a radius that is at least 10 times said thickness of said membrane.

8. The hydrocephalus shunt arrangement according to claim 7, wherein:
said corrugations of said membrane cover at least one-third, at least two-thirds, or at least four-fifths of a portion of said membrane configured to be impinged by a pressure force;

said corrugations are disposed to run annularly;

said corrugations each have different diameters and are disposed concentrically with respect to one another; and each of said corrugations are one of:

circular and do not contact one another, or circular and comprise portions that merge together.

9. The hydrocephalus shunt arrangement according to claim 8, wherein:

said membrane is configured to be moved toward and away from said wall over a movement distance;

said membrane is circular and has a radius that is:

at least 15 times greater than a maximum height of said movement distance, or at most 50 times greater than a maximum height of said movement distance; and said chamber contains a volume that is between 20 cubic millimeters and 350 cubic millimeters.

\* \* \* \* \*